(12) United States Patent
Damarla et al.

(10) Patent No.: US 6,340,484 B1
(45) Date of Patent: Jan. 22, 2002

(54) COMPOSITIONS CONTAINING NEEM SEED EXTRACTS AND SACCHARIDE

(75) Inventors: Sreenivasa Rao Damarla, Kalyananagar; Srinivasa Sridhar; Mambully Chandrasekaran Gopinathan, both of Bangalore, all of (IN)

(73) Assignee: E.I.D. Parry (India) Limited, Bangalore (IN)

( * ) Notice: Subject to any disclaimer, the term of this patent is extended or adjusted under 35 U.S.C. 154(b) by 0 days.

(21) Appl. No.: 09/545,295

(22) Filed: Apr. 7, 2000

(51) Int. Cl.$^7$ ............... A61K 7/00; A61K 31/70; A01N 25/00; A01N 43/16; A01N 43/04

(52) U.S. Cl. .............. 424/761; 424/776; 424/405; 514/453; 514/23; 514/53; 514/54; 514/57

(58) Field of Search ................. 424/195.1, 405, 424/761, 776; 514/453, 23, 53, 54, 57

(56) References Cited

U.S. PATENT DOCUMENTS

| | | | |
|---|---|---|---|
| 3,920,442 A | * | 11/1975 | Albert et al. |
| 4,556,562 A | | 12/1985 | Larson |
| 4,946,681 A | | 8/1990 | Walter |
| 5,001,146 A | | 3/1991 | Carter et al. |
| 5,124,349 A | | 6/1992 | Carter et al. |
| 5,281,618 A | | 1/1994 | Walter |
| 5,352,697 A | | 10/1994 | Butler et al. |
| 5,372,817 A | | 12/1994 | Locke et al. |
| 5,405,612 A | | 4/1995 | Locke et al. |
| 5,409,708 A | | 4/1995 | Locke et al. |
| 5,503,837 A | | 4/1996 | Roland et al. |
| 5,635,193 A | | 6/1997 | Walter |
| 5,653,973 A | * | 8/1997 | Lew et al. |
| 5,695,763 A | | 12/1997 | Kleeberg |
| 5,730,986 A | | 3/1998 | Bandyopadhyay et al. |
| 5,736,145 A | | 4/1998 | Murali |
| 5,827,521 A | | 10/1998 | Moorty |
| 5,856,526 A | | 1/1999 | Sankaram et al. |

FOREIGN PATENT DOCUMENTS

| | | |
|---|---|---|
| EP | 0 579 624 B1 | 3/1992 |
| IN | 181845 | 8/1995 |
| IN | MAS/1855 | 8/1997 |
| WO | WO 92/16109 | 10/1992 |

OTHER PUBLICATIONS

Dimetry, et al., "Synergistic effect of some additives on the biological activity and toxicity of neem-based formulations against the cowpea aphid, Aphis craccivora Koch", Insect Sci. Applic., 17(3/4): 395–99 (1997).

Schauer, "Effects of variously formulated neem seed extracts on *Acrythosiphon pisum* and *Aphis fabae*", Proc. 2$^{nd}$ Int. Neem Conf. (Rauischholzhausen), pp. 141–150 (1983).

Parmar et al., "Neem oil as a synergist for insecticides," Neem Newsletter, 3.(1) (1986), pp 3–5.

Dureja et al., "Stability of Azadirachtin-A in different organic solvents and aqueous solution," Pesticide Research Journal, 11(1):90–92 (1999).

Remhold et al., Azadirachtins: Structure and Activity relations in case of *Epilachna varivestis*, "In" The Neem Tree Azadirachta indica A. Juss. And other meliaceous plants: Sources of unique natural products for integrated pest management, medicine, industry, and other purposes, Ed. Schmutterer, VCH Verlagsgesellschaft, Weinheim (FRG), pp. 222–30 (1995).

Kleenberg et al., "Analytical determination of Azadirachtin A and Azadirachtin B in neem extracts," In: Practice Oriented Results on Use and Production of Neem Ingredients and Pheromones, Proceedings of the 3$^{rd}$ Workshop, Ed. H. Kleeberg, Duck & Graphics, Giessen, pp. 139–148, (1994).

* cited by examiner

*Primary Examiner*—Leon B. Lankford, Jr.
*Assistant Examiner*—Susan D. Coe
(74) *Attorney, Agent, or Firm*—Kilyk & Bowersox, P.L.L.C.

(57) ABSTRACT

A solid pesticide composition is described wherein the composition contains a seem seed extract and at least one saccharide. The solid pesticide composition is preferably storage stable, has higher pesticidal activity, and can be easily dissolved and/or dispersed in a liquid medium, such as a water-based medium.

18 Claims, No Drawings

COMPOSITIONS CONTAINING NEEM SEED EXTRACTS AND SACCHARIDE

BACKGROUND OF THE INVENTION

The present invention relates to compositions containing neem seed extracts such as azadirachtins. The present invention further relates to methods to prepare a stabilized pesticide composition containing neem seed extracts.

Extracts of various parts of the neem tree (*Azadirachta indicia*) such as leaves, bark, seeds, etc. have been long known to have insecticide activity. The seed kernel, in particular, processes the most active limonoids, such as Azadirachtin A and B and structurally related compounds such as C, D, E, F, G, H, I, J, K, and the like, along with nimbin, salannin, azadiradione, and the like. All the natural azadirachtins have reported a very high growth disturbing activity against *Epilachna varivestis*, with $LC_{50}$s in the range of 0.3 to 2.8 ppm (H. Rembold and I. Puhlmann, 1995). More than 100 terpenoid metabolites are reported from the neem seed/fruit of the neem tree. Various methods have been described to extract these active components in the crude or semi crude forms to be used in commercially acceptable vehicles in the form of liquid and solid formulations. The crude neem seed extracts obtained, after removal of lipid components, normally contain about 20–45% by weight of Azadirachtin A and B and have been shown to be potent insect growth regulators and feeding deterrents and are potential active ingredients in commercial pest control formulations. The active molecules, however, of the neem seed extracts are rather large and complex, and having acid and base sensitive functional groups, they tend to be unstable in these vehicles thus posing a major limitation for commercial use of these extracts.

So far azadirachtin has been widely formulated in liquid forms to be applied as an emulsion or solution to agriculture crops. Various organic solvents and other inorganic additives have been used as carriers in order to make a cost effective and efficacious delivery system. The use of such carriers is rather limited, however, since many solvents are deleterious to the stability of azadirachtin. Dureja (1999) has studied the degradation of azadirachtin A in various solvents for 25 days at 29+/−1° C. The results indicated 50% degradation of azadirachtin A in methanol and acetone, 75–80% degradation in methylene chloride, carbon tetrachloride and chloroform, and about 85% degradation in ethanol and water.

Storage-stable azadirachtin formulations and methods of preparing stable azadirachtin compositions have been proposed. U.S. Pat. No. 4,556,562 reports that the stability of azadirachtin in ethanol emulsions increased by diluting the concentration of azadirachtin to between 2000 and 4000 ppm and adjusting the pH to between 3.5 and 6.0. U.S. Pat. No. 4,946,681 (Walter) reports greater stability for azadirachtin in solutions of aprotic solvents containing less than 2–5% of water. U.S. Pat. No. 5,001,146 indicates that azadirachtin stability is improved by adjusting the concentration of the polar aprotic solvent to at least 50% by volume and by decreasing the water content to less than 15% by volume. Moreover, U.S. Pat. No. 5,001,146 further indicates that azadirachtin stability depends upon the type of solvent employed, and that stability requires storage in large quantities of certain enumerated aprotic and alcohol solvents. Murali (U.S. Pat. No. 5,736,145) reports a storage stable aqueous composition containing azadirachtin A and U.S. Pat. No. 5,827,521 indicates a stable azadirachtin formulation containing aliphatic dihydroxylated alcohols of more than 80% by volume and optionally with sunscreens and antioxidants.

U.S. Pat. No. 5,352,697 describes the stability enhancement of azadirachtin in solution by the presence of epoxide, preferably an epoxidized vegetable oil. These methods describe the enhancement of azadirachtin containing extracts in the liquid form prepared from neem seed kernel with organic solvents.

European Patent No. 579,624 describes making an extract of neem seed in solid form with greater stability. The stability of azadirachtin in neem extracts is reported to be improved by removing the lipid impurities from extracts (India Patent Application No. 1855). Walter (U.S. Pat. No. 5,635,193) reports that an azadirachtin containing solid is stable by limiting moisture and volatile polar solvents to less than 1% and 5%, respectively. A formulation containing 0.05% to 2% surfactant and 99% of solid diluent has been claimed as a stable bio-control agent by retention of at least 75% of azadirachtin after 2 weeks of storage at 54° C. Such a formulation may be used as a dust and wettable powder, but the efficacy of azadirachtins in such vehicular formulations is not practically reported.

Another formulation is a solid form of neem seed extract prepared from the kernel of neem seed as per the methods described in U.S. Pat. No. 5,695,763, European Patent No. 579,624, and IN 181,845. The product is quite stable with respect to its active ingredients viz Azadirachtin A, B, nimbin, salannin, and the like.

Though various extracts with stable azadirachtin have been reported, stability of azadirachtin in a formulated state is still a concern. Azadirachtin is highly unstable in various surfactants, organic solvents, and in different combinations of solvents and surfactants in liquid formulations which is a serious limitation for the development of a shelf stable commercial product.

Normal pesticide formulations contain various solvents made mostly from petroleum, and there is a concern that usage of such solvents in specialty pesticide formulations, especially meant for organic farming, veterinary application, and the like, is discouraged. The use of such solvents, even at a lower rate, demands large amounts of surfactants and other additives which makes the cost of the formulations high.

The use of a broader range of ingredients in liquid formulations and the associated problem of instability in such formulations is also a serious concern for the commercial success of azadirachtin containing crop protection agents. Accordingly, there is still a need for a formulation containing simple, safe, and cost effective vehicles which yet provides stable and efficacious products.

As noted above, the pesticidal effect of neem active compounds, such as azadirachtins, is mostly through insect growth regulation, molting inhibition, antifeedant, ovicidal, and other physiological effects and is normally slow compared other synthetic pesticides which result in immediate knockdown. Hence, there is a need to identify ways and methods to enhance the efficacy of neem extracts for their wide spread acceptance as a pesticide.

Accordingly, there is a need to develop environmentally safe pesticide formulations which contain azadirachtin and which are further storage stable, efficacious, and economical.

The aim of the present invention is to develop a delivery system for azadirachtin containing neem seed extracts, free from any organic solvent, and which is completely soluble in water and efficacious at a dosage lower than the normal desired dose of azadirachtin containing neem seed extracts for pest control.

All of the patents and publications mentioned throughout this application are incorporated herein in their entirety.

SUMMARY OF THE INVENTION

A feature of the present invention is to provide a delivery system for neem seed extracts such as azadirachtin and the like, which is preferably free from any organic solvent and completely soluble in water.

Another feature of the present invention is to provide a neem seed extract in solid form which is stable and flowable.

An additional feature of the present invention is to provide a neem seed extract in efficacious solid form which is water soluble and thus is quite easily used to control insect pests.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purpose of the present invention, as embodied and broadly described herein, the present invention relates to a solid pesticide composition comprising neem seed extract comprising azadirachtin and at least one saccharide.

The present invention further relates to a liquid formulation having the above-described solid pesticide composition dissolved and/or dispersed therein.

Further, the present invention relates to a method to increase the pesticidal effectiveness of a composition containing azadirachtin by introducing at least one saccharide into the composition.

It is to be understood that both the foregoing general description and the following detailed description are exemplary and explanatory only and are intended to provide further explanation of the present invention, as claimed.

DETAILED DESCRIPTION OF THE PRESENT INVENTION

The present invention relates to pesticide compositions containing neem seed extracts, such as azadirachtins. In particular, the present invention relates to a solid pesticide composition which contains neem seed extract and at least one saccharide. Preferably, the neem seed extract contains at least azadirachtin. Further, the neem seed extract can contain nimbin, salannin, and/or azadiradione, and the like. The azadirachtin that is preferably present in the neem seed extract can be one or more types of azadirachtin compounds and are more preferable azadirachtin A and/or B but can also be or include structurally related compounds such as azadirachtin D, E, F, H, I and/or K, and the like.

The neem seed extract is present in the pesticide composition in an amount effective to reduce or eliminate insecticidal activity, such as on vegetation. Preferably, the neem seed extract contains from about 0.03 to about 5.0 weight %, and more preferably from about 0.1 to about 1.0 weight % based on the weight of the pesticide composition. Generally, the azadirachtin will be present in the neem seed extract in an amount of from about 20% to about 50% by weight of the neem seed extract, though other amounts below 20% and above 50% are possible. Most preferably, from about 20% to about 50% of the neem seed extract, by weight of the neem seed extract, is an azadirachtin A and/or B.

The neem seed extract can be obtained following the process recited in U.S. Pat. No. 5,695,763 which is incorporated in its entirety by reference herein or using other extraction processes. In general, the azadirachtin is recovered preferably from the seeds of a neem tree by crushing the seeds and then extracting the azadirachtin and other active ingredients from the crushed seeds with water. The extraction of azadirachtin and other active ingredients from the water is preferably accomplished using a non-aqueous solvent which is not miscible with water and has a higher solubility with azadirachtin than water, or by using a surfactant having a turbidity temperature between 20° and 80° C. The concentrated azadirachtin is then recovered from the second extracting solution. The azadirachtin containing solution is then concentrated to produce an azadirachtin concentrate which is added to a liquid hydrocarbon, thus forming an azadirachtin precipitate that is then recovered for use in pesticide formulations. The method described in Indian Pat. No. 181,845 can also be used for the preparation of azadirachtin containing extracts. The azadirachtin can also be recovered by the techniques set forth in U.S. Pat. Nos. 4,556,562 and 5,124, 349 and other conventional methods.

The solubility of such neem extracts (Aza 20–50%) in water is less than 0.1% which can yield 200–500 ppm of azadirachtin in solution. However, the recommended dose of azadirachtin for control of various pest control in the field is about 30 ppm which can be prepared by dissolving 0.06–0.15 g of extracts in 1000 ml of water. But handling such small quantities by the user is cumbersome and can be avoided by formulating/diluting the concentrated extracts in inert carriers. Several diluents such as talc, stealite, soap stone, pyrophyllite and yellow talc, kaolin and related carriers can be used in compositions and formulations, but are unsuitable for azadirachtin based formulations as they may degrade azadirachtin because of their acidity or alkalinity. More particularly, these diluents are not suitable for a water soluble type formulation. In search of alternate diluents, various sugars were studied for their suitability in formulations in terms of stability and other properties of a ready to use formulation. One of the major problems in using sugars, as observed in other pesticide formulations, is the undesired formation of cake type mass of the formulated product during storage due to the hygroscopic nature of these substances. However, unexpectedly, no such problem is encountered with neem seed extracts which may be due to anticaking properties of the fine powdery extracts. A wetting agent, with or with out a sticker, are preferred in preparing the formulation to be used in the field. Two of the compositions (1.25% and 6.12% Aza) of neem seed extracts with sucrose (87.26%) and methyl cellulose (10%) were prepared and their stability evaluated under accelerated conditions at 54° C. The results indicated that the azdirachtin is more stable in the formulation than in the neem seed extract which shows that these saccharides impart an additional stabilizing effect on azadirachtin in the formulated form. In addition to the enhancement of stability, the formulation surprisingly showed higher pesticidal activity, particularly imparting early mortality of the insect larvae. Thus, the present invention provides methods to increase the pesticidal effectiveness of azadirachtin and compositions containing azadirachtin. Further, the present invention provides a method to expedite the mortality rate of compositions containing azadirachtin by introducing an effective amount of at least one saccharide. The present invention also has the ability to increase storage stability of the azadirachtin, improve the growth inhibition of the azadirachtin towards insects, and/or make the mortality rate of an insect and other pesticidal activities occur faster by introducing an effective amount of saccharide. The insect can be in any stage of maturity or development.

With respect to the saccharide, one or more saccharides can be present in the pesticide composition. Preferably at least two different saccharides are present in the pesticide composition. More preferably, at least one saccharide is a di-saccharide and at least one other saccharide is a polysaccharide. Even more preferably, the saccharides present in the preferred pesticide composition is at least one di-saccharide and a cellulose derivative, such as methyl cellulose. The mono-saccharide is preferably a simple sugar, such as glucose, fructose, and/or galactose. The saccharide can also be a di-saccharide such as sucrose. Most preferably, the saccharide is a methyl cellulose and a sucrose. The saccharides are preferably present in an amount of from about 20% to about 99.9% by weight of the pesticide composition. More preferably, this saccharide is present in an amount of from about 70 weight % to about 80 weight %.

Most preferably, the saccharide is a cellulose derivative such as a methyl cellulose which is present from about 0.1 to about 20 weight % by weight of the pesticide composition and the disaccharide, such as sucrose, is present in an amount of from about 0.5% to about 90% by weight of the pesticide composition.

If desired, carriers such as conventional sticking agents, like natural polymers, for example gum arabic, guar gum, polyvinyl cellulose and the like, in the form of powders, granules, or lattices can be used in the compositions to improve the adherence of the pesticide.

The ingredients forming the pesticide composition may be combined after the ingredients are intimately ground to a particle size of 10–100μ and mixed together by blending, preferably mechanically, to result in a free flowing powder. Alternatively, the neem seed extracts may be dissolved in a suitable organic solvent and the solution combined with saccharides and then the solvents removed, such as being stripped off under vacuum. The mixture is then intimately ground to a particle size, such as to a range of from 10–100μ, and mixed together such as by blending. It is believed that the azadirachtin present further serves to prevent any caking of the saccharides in the pesticide composition.

The solid pesticide composition is preferably in powder form but can be present in other solid forms such as pellets and the like, and is preferably stable for long periods of time. For instance, the solid pesticide compositions of the present invention can maintain at least 90% by weight of the azadirachtins originally present even after four weeks of storage at 54° C. in a sealed container. Accordingly, the pesticide compositions of the present invention are storage stable.

More advantageously, the solid pesticide compositions of the present invention can be easily formed into a liquid formulation by introducing the solid pesticide composition into a liquid medium. The liquid medium is preferably a water-based solution such as water. The liquid medium can also contain other ingredients such as from about 1% to about 5% by weight of the pesticide composition are possible with the present invention. However, a concentration of about 0.0065% by weight of the pesticide may be sufficient for most of the applications.

The pesticide compositions of the present invention can also include conventional additives, such as carriers, biocides, anti-foamers, and the like.

The pesticide compositions of the present invention can be used in any suitable form, such as, but not limited to, dispersions, suspensions, dusting powders, granules, baits, aerosols, fumigating release devices, powders, pellets, and the like.

The present invention will be further clarified by the following examples, which are intended to be purely exemplary of the present invention.

EXAMPLES

1. Preparation of Azadirachtin Formulations

The dry neem seed extracts of azadirachtin were prepared according to the method described in the Indian Patent No. 181, 845. The samples were pale yellow free flowing powders and contained about 30–45% by weight of azadirachtin (A, 25–35% and B, 5–9%). One of the samples (I) containing 45.02% by weight of azadirachtin (A, 36.16% and B, 8.86%) was used in the preparation of the following formulations. Analysis of azadirachtin content of all the samples and formulations was by HPLC, using an external analytically pure azadirachtin standard, as per the method described by Kleeberg (1994).

Formulation 1: 2.74 g of the neem seed extract powder containing azadirachtin (45.02%) was added to 87.26 g of finely powdered sucrose and 10 g of methyl cellulose and mixed thoroughly in a blender for 5–10 minutes. The azadirachtin content of the formulation was 1.25% by weight (Aza A 1.01%, Aza B 0.24%).

Formulation 2: 13.4 g of the dry neem seed extract powder containing azadirachtin (45.02%) was added to 71.3 g of finely powdered sucrose and 10 g of methyl cellulose and mixed thoroughly in a blender for 5–10 minutes. The azadirachtin content of the formulation was 6.11% (Aza A 4.93, Aza B 1.18).

2. Stability of Azadirachtin in Solid Neem Seed Extract (I) and its Formulations 1 and 2

The stability of the neem seed extract (I) and its formulations 1 & 2 obtained by the methods described in Example 1 was studied at 54° C. Each of the samples (20 g) was placed into a sealed glass vial and kept in an incubator at 54° C. for 28 days. Samples were taken out every week and analyzed for their azadirachtin content by HPLC. The results (Table 1) indicate higher stability for azadirachtin in formulations 1 & 2 compared to that of neem seed extract (I) [control].

TABLE 1

| Sl. No. | Sample/ Formulation | Initial Aza Content (%) | | % Retention of Azadirachtin | | | | | |
| --- | --- | --- | --- | --- | --- | --- | --- | --- | --- |
| | | | | 7 Days | | 14 Days | | 28 Days | |
| | | Aza A | Aza B | Aza A | Aza B | Aza A | Aza B | Aza A | Aza B |
| 1 | I | 36.16 | 8.86 | 91.32 | 93.46 | 86.44 | 91.75 | 83.49 | 90.07 |
| 2 | 1 | 1.01 | 0.24 | 93.07 | 95.83 | 93.07 | 95.83 | 90.10 | 95.83 |
| 3 | 2 | 4.93 | 1.18 | 93.31 | 95.76 | 92.49 | 94.92 | 88.44 | 94.92 |

I = Neem Seed extract
1 = Solid neem seed extract (2.74%), Methocel (10%), Sucrose (87.26%)
2 = Solid neem seed extract (13.4%), Methocel (10%), Sucrose (76.6%)

3. Antifeedant Efficacy of Neem Extract Containing Azadirachtin and its Formulation Containing Sucrose Against *Spodoptera litura*

The solid neem seed extract containing azadirachtin (I) and its formulation 1 were tested for their antifeedant effect against the insect *Spodoptera litura*. The castor leaf disks were cut and dipped in 10, 30 and 50 ppm of azadirachtin concentrations of each test sample and offered to 5 day old *S. litura* larvae. The experiments were replicated thrice with ten insects per treatment per replication. The percentage antifeedency was assessed after 2, 5, 7, 10 and 14 days after treatment by calculating the difference in leaf area consumed in the treated and control group. The antifeedant effect of both the sample was found almost comparable.

TABLE 2

| Treatment | Days After | Formulation efficacy, % Antifeedance | |
|---|---|---|---|
| Aza, (ppm) | Treatment | I | 1 |
| 10 | 2 | 52.01 | 63.80 |
|  | 5 | 91.00 | 88.53 |
|  | 7 | 93.41 | 91.43 |
|  | 10 | 95.39 | 94.04 |
| 30 | 2 | 52.40 | 50.59 |
|  | 5 | 93.56 | 81.77 |
|  | 7 | 96.56 | 90.50 |
|  | 10 | 98.37 | 95.23 |
| 50 | 2 | 60.39 | 53.84 |
|  | 5 | 95.03 | 86.67 |
|  | 7 | 97.49 | 93.01 |
|  | 10 | 99.00 | 96.54 |

I = Neem Seed extract
1 = Solid neem seed extract (2.74%), Methocel (10%), Sucrose(87.26%)

4. Growth Inhibition Efficacy of Neem Extract Containing Azadirachtin and its Formulation Containing Sucrose Against *Spodoptera litura*

The solid neem seed extract containing azadirachtin (I) and its formulation 1 were tested for their growth inhibition effect against the insect *Spodoptera litura*. The castor leaves treated with 10, 30 and 50 ppm of azadirachtin concentration of various formulations were offered to 5 day old *S. litura* larvae. The experiments were conducted using ten insects per treatment and replicated thrice. Growth inhibition was assessed on 2, 5, 7, 10 and $14^{th}$ day after treatments by weighing the larvae and the mean weights for each treatment group were expressed as a percentage of controls. The formulation 1 containing sucrose shown prolongation of larval stages up to 14th day compared to neem seed extract (Table 3).

TABLE 3

| Treatment | Days After | Formulation efficacy, % Growth Inhibition | |
|---|---|---|---|
| Aza, ppm | Treatment | I | 1 |
| 10 | 2 | 48.85 | 26.50 |
|  | 5 | 84.90 | 78.96 |
|  | 7 | 90.13 | 88.30 |
|  | 10 | * | 88.15 |
|  | 14 | * | 93.00 |
| 30 | 2 | 36.91 | 10.67 |
|  | 5 | 89.18 | 70.59 |
|  | 7 | 93.71 | 86.49 |
|  | 10 | * | 97.84 |
|  | 14 | * | 100.0 |
| 50 | 2 | 47.11 | 13.00 |
|  | 5 | 91.96 | 78.30 |
|  | 7 | 96.87 | 89.84 |

TABLE 3-continued

| Treatment | Days After | Formulation efficacy, % Growth Inhibition | |
|---|---|---|---|
| Aza, ppm | Treatment | I | 1 |
|  | 10 | * | 97.11 |
|  | 14 | * | 100.0 |

I = Neem Seed extract
1 = Solid neem seed extract (2.74%), Methocel (10%), Sucrose (87.26%)
*Insects entered into pupation stage.

5. Efficacy of Neem Extract Containing Azadirachtin and its Formulation Containing Sucrose Against Mortality of *Spodoptera litura*

The insecticidal (mortality) activity of the solid neem seed extract containing azadirachtin (I) and its combination with sucrose (1) were studied against the insect *Spodoptera litura*. For the mortality test, castor leaves treated with 10, 30 and 50 ppm concentrations of azadirachtin of test samples, I and 1, were offered to 5 day old *S. litura* larvae. The experiments were replicated thrice with 10 insects per treatmment per replication. The percentage mortality was assessed after 5, 7, 10 and $14^{th}$ day after treatment. The efficacy data (Table 4) indicates that the formulation containing sucrose showed higher mortality even at 10 ppm of Aza against the insect *Spodoptera litura*.

TABLE 4

| Treatment | | Formulation Efficacy, % Mortality | |
|---|---|---|---|
| Aza, ppm | Days after treatment | I | 1 |
| 10 | 5 | 10.00 | 10.00 |
|  | 7 | 16.67 | 36.67 |
|  | 10 | 56.67 | 76.67 |
|  | 14 | 47.62 | 88.89 |
| 30 | 5 | 30.00 | 20.00 |
|  | 7 | 50.00 | 63.33 |
|  | 10 | 86.67 | 96.67 |
|  | 14 | 91.67 | 100.0 |
| 50 | 5 | 60.00 | 30.00 |
|  | 7 | 76.67 | 70.00 |
|  | 10 | 100.0 | 93.33 |
|  | 14 | 100.0 | 100.0 |

I = Neem Seed extract
1 = Solid neem seed extract (2.74%), Methocel (10%), Sucrose (87.26%)

Other embodiments of the present invention will be apparent to those skilled in the art from consideration of the specification and practice of the invention disclosed herein. It is intended that the specification and examples be considered as exemplary only, with a true scope and spirit of the present invention being indicated by the following claims and equivalents thereof.

What is claimed is:

1. A solid pesticide composition comprising at least one saccharide and a neem seed extract, wherein said neem seed extract comprises azadirachtin, wherein said composition is a free flowing powder, and wherein said saccharide and said neem seed extract are not chemically bonded.

2. The solid pesticide composition of claim 1, wherein said composition is storage stable.

3. The solid pesticide composition of claim 1, wherein said composition retains at least 90% of said azadirachtins present after four weeks of storage at 54° C. in a sealed container.

4. The solid pesticide composition of claim 1, wherein said saccharide comprises di-saccharide.

5. The solid pesticide composition of claim 1, wherein said saccharide is at least one polysaccharide.

6. The solid pesticide composition of claim 1, wherein said saccharide is a cellulose derivative.

7. The solid pesticide composition of claim 1, wherein said saccharide is a methyl derivative of cellulose.

8. The solid pesticide composition of claim 1, wherein said saccharide is a methylcellulose.

9. The solid pesticide composition of claim 1, wherein said saccharide is at least one disaccharide and at least one polysaccharide.

10. The solid pesticide composition of claim 1, wherein said saccharide is a monosaccharide, di-saccharide, a polysaccharide, or mixtures thereof.

11. The solid pesticide composition of claim 1, wherein said azadirachtin is present in an amount of from about 0.03 to about 5 weight % based on the weight of the solid pesticide composition.

12. The solid pesticide composition of claim 1, wherein said azadirachtin is an azadirachtin A, an azadirachtin B, or both.

13. The solid pesticide composition of claim 1, wherein said azadirachtin A, azadirachtin B, or mixtures thereof are present in an amount of from about 20% to about 50% by weight of said neem seed extract.

14. The solid pesticide composition of claim 1, wherein said saccharide is present in an amount of from about 20% to about 99.9 weight % based on the weight of the solid pesticide composition.

15. A liquid pesticide composition comprising the solid pesticide composition of claim 1 present in a liquid medium.

16. The liquid pesticide formulation of claim 15, wherein said liquid medium is a water-based medium.

17. A solid pesticide composition comprising at least one saccharide and azadirachtin, wherein said composition is a free flowing powder and wherein said saccharide and said azadirachtin are not chemically bonded.

18. The solid pesticide composition of claim 1, wherein said pesticide composition is formed by mixing at least one saccharide and a neem seed extract together.

* * * * *